United States Patent [19]

Commandeur et al.

[11] Patent Number: 5,181,992
[45] Date of Patent: Jan. 26, 1993

[54] SEPARATION OF ISOMERS, E. G., PHENETHYL BROMIDE FROM 1-PHENYL-1-BROMOETHANE

[75] Inventors: Raymond Commandeur, Vizille; Gilles Drivon, Saint-Martin en Haut; Elie Ghenassia, Grenoble, all of France

[73] Assignee: Atochem, Puteaux, France

[21] Appl. No.: 537,926

[22] Filed: Jun. 13, 1990

[30] Foreign Application Priority Data

Jun. 13, 1989 [FR] France ................. 89 07800

[51] Int. Cl.$^5$ .............................. B01D 3/34
[52] U.S. Cl. ................. 203/29; 203/DIG. 6; 570/211; 585/462; 585/833
[58] Field of Search ............ 203/29, DIG. 6; 570/194, 211; 585/462, 463, 465, 459, 835, 833

[56] References Cited

U.S. PATENT DOCUMENTS

| | | | |
|---|---|---|---|
| 2,246,762 | 6/1941 | Schirm | 585/462 |
| 2,746,938 | 5/1956 | Ehm et al. | 536/119 |
| 3,058,892 | 10/1962 | Plesmid | 203/29 |
| 3,453,339 | 7/1969 | Ransley | 570/194 |
| 4,219,652 | 8/1980 | Zimmerman et al. | 546/144 |
| 4,321,383 | 3/1982 | Sprague | 546/113 |

*Primary Examiner*—Virginia Manoharan
*Attorney, Agent, or Firm*—Burns, Doane, Swecker & Mathis

[57] ABSTRACT

Mixtures of isomers, e.g., mixtures of phenethyl bromide and 1-phenyl-1-bromoethane, are separated by (a) selectively condensing one such isomer with an aromatic compound bearing at least one aryl (nuclear) hydrogen atom, e.g., xylene, in the presence of a catalytically effective amount of a Friedel-Crafts catalyst, e.g., ferric chloride, and then (b) separating the product of condensation, e.g., phenylxylylethane, from the unreacted isomer.

7 Claims, No Drawings

SEPARATION OF ISOMERS, E. G., PHENETHYL BROMIDE FROM 1-PHENYL-1-BROMOETHANE

BACKGROUND OF THE INVENTION

1. Field of the Invention

The present invention relates to a process for the separation of two isomers and to the application of such process for the purification of 1-phenyl-2-bromoethane.

2. Description of the Prior Art

1-Phenyl-2-bromoethane ($C_6H_5$—$CH_2$—$CH_2Br$), or phenethyl bromide, is a known intermediate used in a variety of organic syntheses; it is prepared by the free radical hydrobromination of styrene with gaseous hydrobromic acid:

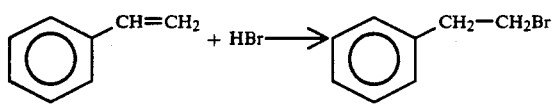

This anti-Markovnikov-type addition is promoted by the simultaneous introduction of air and gaseous HBr into styrene dissolved in a slightly polar inert solvent, such as carbon tetrachloride. The Markovnikov-type addition:

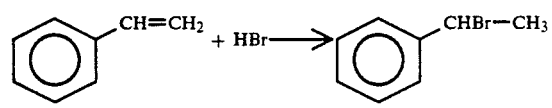

competes with the first reaction, which is never totally selective, the significance of said competing reaction increasing with the concentration of styrene in $CCl_4$. This reaction is, moreover, promoted by the presence of metallic impurities, such as iron.

The separation of phenethyl bromide from its -bromo-1-phenylethane isomer is difficult to accomplish by distillation in view of the small difference in the respective boiling points: 217° C. for phenethyl bromide and 203° C. for 1-bromo-1-phenylethane.

U.S. Pat. No. 3,058,892 describes treating the mixture of phenethyl bromide and its isomer with zinc oxide at a temperature ranging from 100° C. to 150.C in order to selectively decompose the isomer. It is recommended to minimize the temperature and the reaction time in order to prevent the decomposition of the phenethyl bromide.

SUMMARY OF THE INVENTION

Accordingly, a major object of the present invention is the provision of an improved process for the separation of phenethyl bromide from admixture thereof with its 1-bromo-1-phenylethane isomer, which improved process comprises selectively condensing said 1-bromo-1-phenylethane isomer with another compound to produce a heavy condensate that is easily removed by distillation.

Another object of this invention is the provision of an improved process for the selective separation of a variety of isomeric systems that can be carried out at lower temperatures than the prior art separations.

Briefly, the present invention features a process for the separation of two isomers of the formulae:

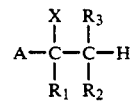

and

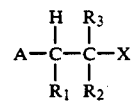

in which A is an aryl radical or a substituted aryl radical; X is a halogen atom; $R_1$ is $X_1$, hydrogen or an alkyl radical; $R_2$ is $X_2$, H or an alkyl radical; $X_1$ and $X_2$ are also halogen atoms; and $R_3$ is hydrogen or an alkyl radical, comprising:

(a) condensing the isomer (I) with a compound bearing at least one aryl (nuclear) hydrogen, in the presence of a catalytically effective amount of a Friedel-Crafts catalyst; and (b) then separating the resulting condensation product from said isomer (II).

DETAILED DESCRIPTION OF THE PREFERRED EMBODIMENTS OF THE INVENTION

More particularly according to the present invention, the two isomers (I) and (II) are produced, for example by the addition reaction of a hydrogen halide with a compound of the formula:

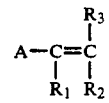

wherein A, $R_1$, $R_2$ and $R_3$ are as defined above.

Advantageously, A is a radical derived from benzene, biphenyl, naphthalene or anthracene. A can be substituted by halogen atoms or $NO_2$, CN, alkyl or alkoxy groups.

Preferably, X, $X_1$ and $X_2$ are chlorine or bromine atoms.

$R_1$, $R_2$ and $R_3$ are also alkyl radicals; these alkyl radicals can have up to 4 carbon atoms. Preferably, the isomers (I) and (II) are such that A is phenyl or substituted phenyl, $R_1$ and $R_2$ are alkyl radicals having up to 4 carbon atoms and $R_3$ is hydrogen.

The isomer (I) is subjected to a condensation reaction by contacting the mixture with a compound bearing at least one aryl hydrogen. Any such compound will suffice, provided that it bears a sufficiently mobile nuclear hydrogen atom and that it reacts with the isomer (I) with elimination of HX. Aromatic hydrocarbons, aromatic ethers and phenol are advantageously used. Exemplary such aromatic hydrocarbons include benzene, toluene, ethylbenzene, cumene and the xylenes.

A representative aromatic ether is phenyl methyl ether ($C_6H_5$—O—$CH_3$).

It is also within the scope of the invention to use a mixture of aromatic hydrocarbons or of aromatic ethers, or any combination of these compounds.

The isomers (I) and (II) can comprise a simple admixture thereof, or they can be dissolved in a solvent therefor. The Friedel-Crafts catalyst is known, per se. The following are termed Friedel-Crafts catalysts: Lewis acids (metal halides, etc.), protonic acids and zeolites. Exemplary of the metal halides, ferric chloride and aluminum chloride are representative. Exemplary protonic acids include the oxyacids such as sulfuric acid and paratoluenesulfonic acid. And exemplary zeolites include the decationized X or Y faujasites.

For purposes of illustration, in a mixture of phenethyl bromide ($C_6H_5$—$CH_2$—$CH_2Br$) and 1-phenyl-1-bromoethane ($C_6H_5$—$CHBr$—$CH_3$), only the latter undergoes a condensation reaction with meta-xylene to form phenylxylylethane in accordance with the reaction:

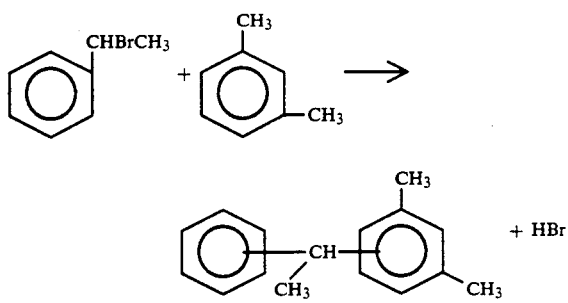

The phenylxylylethane thus formed has a high boiling point (higher than 300° C.) and therefore does not present any problem in separating it from phenethyl bromide (boiling point 217° C.) by distillation.

The amount of catalyst can vary over wide limits; for example, 0.5 to 2 g of $FeCl_3$ can be used per kg of phenethyl bromide.

The temperature can also vary over wide limits; advantageously, it is within a temperature range in which the isomers and the compound with which the condensation reaction is carried out are liquid. It is preferred to carry out the reaction at a temperature ranging from 50° to 100° C. The temperature is also selected such that the condensation reaction can be carried out at atmospheric pressure or at a pressure which does not exceed a few bars.

The reaction time advantageously ranges from a few minutes to 2-3 hours; this reaction time decreases with increasing temperatures.

If the isomers are already dissolved in a solvent, such as an aromatic hydrocarbon, an ether having an aromatic moiety or phenol, it suffices to add the catalyst to this mixture in order to conduct the process of the invention.

After step (a) of the subject process, i.e., the condensation reaction, the reaction mixture can be washed with an aqueous solution of hydrochloric acid. Step (b), i.e., the separation to recover isomer (II), is then carried out. Any technique can be used therefor, but distillation is the preferred.

In order to further illustrate the present invention and the advantages thereof, the following specific examples are given, it being understood that same are intended only as illustrative and in nowise limitative.

EXAMPLE 1

The reaction was carried out in the following apparatus:

(i) 1-liter conical flask with tapping;
(ii) thermometric casing with thermocouple;
(iii) nitrogen blanket;
(iv) ascending condenser filled with water;
(v) water bubbler.

370 g of crude phenethyl bromide having the composition indicated in Table I and 212 g of a mixture of isomers of xylene (commercial product rich in the metaisomer) were charged into the conical flask. 0.5 g of anhydrous ferric chloride was then added and the entire mass was brought to 60° C. while sweeping with nitrogen.

The stream of gas passed into the water bubbler and the hydrobromic acid formed was determined continuously using sodium hydroxide solution in the presence of phenolphthalein. The amount of HBr liberated (0.165 mole) essentially corresponded to the amount of 1-phenyl-1-bromoethane (0.153 mole).

Moreover, chromatographic analysis carried out on a sample withdrawn upon completion of a reaction time of 5 hours, 10 min (see Table I) evidenced the complete disappearance of 1-phenyl-1-bromoethane.

The same analysis carried out after 6 hours, 40 min, evidenced that there was virtually no change in the mixture. There was no reduction in the phenethyl bromide content, namely, the product was stable under these conditions (the samples were washed immediately with water+10% HCl before carrying out the analysis).

At the end of the experiment, the entire reaction mixture was washed with 10% hydrochloric acid and then with water. The organic phase was then placed in a distillation flask surmounted by a five-plate column and was then subjected to an azeotropic drying operation under vacuum in such a manner as to maintain the temperature in the flask at about 80° C. Upon completion of drying, a reflux head was installed on the distillation column and the contents of the flask were distilled under progressive vacuum with a slight reflux. The distillation fraction passing over at a temperature of from 101° to 103° C. under 15 mm of mercury (see analysis in Table I) represented 90% of the amount of phenethyl bromide present in the starting material. The bottoms temperature was 170° C. upon completion of distillation and no decomposition was determined.

The phenyl bromide thus obtained (colorless) had a purity greater than 98.5%. It could be provided with a higher degree of purity, by refining the distillation. Indeed, in consideration of its clearly higher boiling point, 1,2-dibromoethylbenzene could be separated off easily.

On the other hand, upon examining the results reported in the Table, it will be seen that certain products other than 1-phenyl-1-bromoethane disappeared or decreased (peaks 7, 12 and 14). These unidentified products probably possessed a reactive bromine atom which would be an instability factor during a distillation of crude phenethyl bromide, not having been subjected to the treatment described immediately above. 1-Phenyl-1-bromoethane underwent a condensation reaction with xylene to form phenylxylylethane.

TABLE I (results of Example 1):

|  | Crude phenethyl bromide | Xylenes | Mixture of phenethyl bromide + xylenes before reaction | Samples withdrawn after a reaction time of 5 hours, 10 min | Samples withdrawn after a reaction time of 6 hours, 40 min | Phenethyl bromide distilled | Distillation residue |
|---|---|---|---|---|---|---|---|
| 1 | 0.45 | 0.49 | 0.62 | 0.52 | 0.57 | 0.57 | — |
| 2 | 0.45 | — | 0.25 | 0.09 | 0.09 | — | — |
| 3 | — | 0.98 | 0.77 | 0.65 | 0.66 | 0.14 | — |
| 4 (Ethylbenzene) | — | 21.61 | 8.57 | 10.69 | 10.66 | — | — |
| 5 (m + p-xylene) | 0.39 | 69.49 | 36.77 | 30.10 | 29.64 | — | — |
| 6 (ortho-xylene) | — | 7.16 | 3.73 | 4.47 | 4.38 | — | — |
| 7 | 0.30 | — | 0.22 | — | — | x | — |
| 8 (1-bromo-1-phenylethane) | 7.63 | — | 3.29 | — | — | — | — |
| 9 (phenethyl bromide) | 80.29 | — | 41.06 | 41.86 | 41.99 | 98.76 | 0.98 |
| 10 (1,2-dibromoethylbenzene) | 7.51 | — | 3.13 | 3.46 | 3.40 | 0.53 | 22.44 |
| 11 phenylxylylethane) | — | — | 0.26 | 4.77 | 4.79 | — | 37.64 |
| 12 | 0.81 | — | 0.40 | x | x | — | x |
| 13 | 0.75 | — | 0.33 | 0.56 | 0.57 | — | 4.49 |
| 14 | 0.83 | — | 0.28 | x | — | — | 0.48 |
| 15 | 0.58 | — | 0.32 | 0.32 | 0.32 | — | Σ 4.41 |
| 16 | — | — | — | 1.24 | 1.45 | — | 12.57 |
| 17 | — | — | — | 1.27 | 1.48 | — | 12.51 |
| 18 | — | — | — | x | x | — | 3.69 |

"x" denotes trace amounts;
The numbers in the first column indicate the exit order on the chromatogram;
Products 1 to 3 were lightweight and products 12 to 18 were heavy;
The compositions are in surface percentage of the products eluted by chromatography;
"10" is also termed 1,2-dibromo-1-phenylethane.

EXAMPLE 2

A mixture of:
(i) 72.6% of ethylbenzene;
(ii) 25.8% of 1-chloro-1-phenylethane; and
(iii) 1.6% of 2-chloro-1-phenylethane was treated in the same apparatus as in Example 1.

The mixture was introduced over the course of 1 hour, 30 min, into 12.6 moles of ethylbenzene, at 70° C., containing 1.64 g of anhydrous FeCl₃.

The reaction mixture was then maintained at 70° C. for an additional 3 hours. Chromatographic analysis carried out on various samples, after the entirety of the mixture had been introduced until the experiment was terminated, evidenced:

(1) the very rapid disappearance of 1-chloro-1phenylethane;
(2) the absence of reaction of 2-chloro-1phenylethane.

EXAMPLE 3

370 g of crude phenethyl bromide having the composition indicated in Table II and 85 g of toluene were charged into an apparatus identical to that of Example 1. 0.12 g of anhydrous ferric chloride was then introduced and the entire mass was brought from 85° to 125° C. while sweeping the reaction zone with nitrogen. The stream of gas passed into the water bubbler and the hydrobromic acid formed was determined continuously. The amount of HBr liberated upon completion of the reaction was 0.451 mole.

Moreover, chromatographic analysis (see Table II) evidenced the very rapid disappearance of 1-bromo-1-phenylethane and the progressive disappearance of 1,2-dibromoethylbenzene (or 1,2-dibromo-1-phenylethane). In contrast, the content of phenethyl bromide did not change over the entire treatment period. The reaction mixture treated in the same manner as in Example 1 provided, after distillation, a phenethyl bromide having a purity greater than 99.5%, with a yield of 90% relative to the amount of starting material.

TABLE II

|  | | CHANGE IN THE COMPOSITION | | | |
|---|---|---|---|---|---|
|  | Crude phenethyl | After a reaction time of 1 h | After a reaction time of 2 h | After a reaction time of 4 h, 45 min | After a reaction time of 5 h, 45 min |
| 1) | 0.42 | 0.39 | 0.38 | 0.34 | 0.49 |
| 2) | — | 0.14 | 0.14 | — | — |
| 3) Toluene | | 22 | 22 | 20.55 | 21.04 |
| 4) 1-Bromo-1-phenylethane | 7.59 | — | — | — | — |
| 5) Phenethyl bromide | 80.66 | 60.36 | 61.58 | 64.68 | 67.38 |
| 6) 1,2-Dibromoethylbenzene | 7.77 | 4.76 | 3.41 | 1.54 | X |
| 7) Phenyltolylethane | | 4.33 | 4.33 | 4.45 | 4.40 |
| 8) | 0.36 | 0.65 | 0.59 | 0.58 | 0.65 |
| 9) | 0.38 | 0.74 | 0.62 | 0.57 | 0.56 |
| 10) | 0.83 | — | — | — | — |
| 11) | | X | 0.31 | 0.41 | — |
| 12) | | 0.54 | 0.91 | 0.94 | — |
| 13) | 0.72 | 1 | 0.88 | 1.03 | 1.07 |
| 14) | | 0.34 | 0.40 | 0.70 | 1.11 |

TABLE II-continued

| | Crude phenethyl | CHANGE IN THE COMPOSITION | | | |
|---|---|---|---|---|---|
| | | After a reaction time of 1 h | After a reaction time of 2 h | After a reaction time of 4 h, 45 min | After a reaction time of 5 h, 45 min |
| 15) | | 0.23 | 0.18 | X | X |
| 16) | | 2.84 | 2.73 | 2.76 | 2.53 |

The compositions are given in surface percentage of the products eluted by chromatography;
— indicates "not detected";
X indicates "trace" amounts.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the separation of two isomers of the formulae (I) and (II):

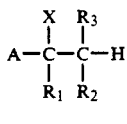

(I)

and

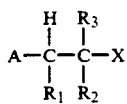

(II)

in which A is an aryl radical or a substituted aryl radical; X is a halogen atom; $R_1$ is $X_1$, hydrogen or an alkyl radical; $R_2$ is $X_2$, H or an alkyl radical; $X_1$ and $X_2$ are also halogen atoms; and $R_3$ is hydrogen or an alkyl radical, comprising:

(a) condensing the isomer (I) with an aromatic compound bearing at least one aryl hydrogen, in the presence of a catalytically effective amount of a Friedel-Crafts catalyst; and (b) separating the product of condensation of step (a) from the isomer (II).

2. The process as defined by claim 1, wherein said formulae (I) and (II), A is phenyl or substituted phenyl, $R_1$ and $R_2$ are alkyl radicals having up to 4 carbon atoms, $R_3$ is hydrogen and X, $X_1$ and $X_2$ are chlorine or bromine atoms.

3. The process as defined by claim 1, said aryl hydrogen compound comprising an aromatic hydrocarbon, aromatic ether or phenol.

4. The process as defined by claim 1, said Friedel-Crafts catalyst comprising ferric chloride 5. The process as defined by claim 1, said isomer (II) comprising phenethyl bromide.

6. The process as defined by claim 1, said aryl hydrogen compound comprising benzene, toluene, ethylbenzene, cumene or a xylene.

7. The process as defined by claim 1, comprising distilling the isomer (II) from the condensation reaction medium.

* * * * *